(12) United States Patent
Popescu et al.

(10) Patent No.: US 8,009,796 B2
(45) Date of Patent: Aug. 30, 2011

(54) X-RAY CT SYSTEM TO GENERATE TOMOGRAPHIC PHASE CONTRAST OR DARK FIELD EXPOSURES

(75) Inventors: Stefan Popescu, Erlangen (DE); Christian David, Lauchringen (DE); Tilman Donath, Brugg (CH); Eckhard Hempel, Fuerth (DE); Martin Hoheisel, Erlangen (DE); Franz Pfeiffer, Brugg (CH)

(73) Assignees: Siemens Aktiengesellschaft, Munich (DE); Paul Scherrer Institut (CH)

( * ) Notice: Subject to any disclaimer, the term of this patent is extended or adjusted under 35 U.S.C. 154(b) by 79 days.

(21) Appl. No.: 12/566,053

(22) Filed: Sep. 24, 2009

(65) Prior Publication Data

US 2010/0080341 A1  Apr. 1, 2010

(30) Foreign Application Priority Data

Sep. 24, 2008  (DE) .......................... 10 2008 048 688

(51) Int. Cl.
*A61B 6/03* (2006.01)
(52) U.S. Cl. .......................................... 378/19
(58) Field of Classification Search ............ 378/19, 378/4

See application file for complete search history.

(56) References Cited

U.S. PATENT DOCUMENTS

| 2007/0153979 A1 | 7/2007 | Baumann et al. |
| 2007/0183562 A1 | 8/2007 | Popescu et al. |
| 2007/0183583 A1* | 8/2007 | Baumann et al. ............. 378/145 |

FOREIGN PATENT DOCUMENTS

| EP | 1 731 099 | 12/2006 |
| WO | WO 2007/074029 | 7/2007 |

OTHER PUBLICATIONS

"Hard-X-Ray Dark-Field Imaging Using a Grating Interferometer," Pfeiffer et al, Nature Materials, vol. 7 (2008) pp. 134-137.

* cited by examiner

*Primary Examiner* — Chih-Cheng G Kao
(74) *Attorney, Agent, or Firm* — Schiff Hardin LLP

(57) ABSTRACT

An x-ray CT system that generates tomographic phase contrast or dark field exposures, has at least one grating interferometer with three grating structures arranged in series in the radiation direction, with a modular design of the second and third grating structures. The distance between the first grating structure of the x-ray source and the second grating structure (fashioned as a phase grating) of the respective grating/detector modules is adapted, depending on the fan angle, corresponding to a period of the grating structure of the x-ray source projected onto the grating detector module at a respective fan angle ($\phi_i$).

13 Claims, 3 Drawing Sheets

X-RAY CT SYSTEM TO GENERATE TOMOGRAPHIC PHASE CONTRAST OR DARK FIELD EXPOSURES

BACKGROUND OF THE INVENTION

1. Field of the Invention

The invention concerns an x-ray computed tomography (CT) system of the type having a source/detector system to generate tomographic phase contrast or dark field exposures, the source/detector system being arranged on a gantry that can rotate around a system axis.

2. Description of the Prior Art

An x-ray CT system for generating tomographic phase contrast or dark field exposures is known that has a source/detector system mounted on a gantry for rotation around a system axis. The source/detector system of this known x-ray CT system has an x-ray source and a detector arrangement. The x-ray source has a grating structure that emits bands of emission maxima and emission minima of a generated x-ray radiation with a grating period, the bands are arranged like a grating, so a beam fan of x-rays expanding in two planes arises with a maximum fan angle in the rotation plane of the gantry and a Z-angle perpendicular to the rotation plane of the gantry, The detector arrangement has a number of grating/detector modules arranged parallel to one another, each module having arranged one after the other in the beam direction):

at least one phase grating that generates an interference pattern, and an analysis grating with a directly connected detector with a number of detector elements to determine phase, average radiation intensity and amplitude of the average intensity of the radiation per detector element given relative displacement of one of the upstream grating structures, with the grating lines of all grating structures aligned parallel to one another and parallel to the system axis.

Such an x-ray CT system with modular design of the source/detector system composed of a number of grating detector modules that are operated as a Talbot interferometer is known from the disclosure document DE 10 2006 015 358 A1. The geometric conditions that are necessary for the arrangement of the grating structures in order to be able to achieve reasonable measurement results are also described therein. Such geometric conditions include:

$$p_0 = p_2 \times \frac{1}{d},$$

$$p_1 = 2 \times \frac{p_0 \times p_2}{p_0 + p_2}$$

$$d = \frac{1 \times d^=}{1 \times d^=} \text{with } d^= = \frac{1}{2} \times \left(\frac{p_1^2}{4\lambda}\right),$$

$$h_1 = \frac{\lambda}{2(n-1)}$$

wherein $p_0$=hereby means the grating period of the source grating $G_0$,
$p_1$=hereby means the grating period of the phase grating $G_1$,
$P_2$=hereby means the grating period of the analysis grating $G_2$,
d=distance of the phase grating $G_1$ from the analysis grating $G_2$ in the fan beam geometry,
$d^=$=distance of the phase grating $G_1$ from the analysis grating $G_2$ under parallel geometry,
I=distance of the source grating $G_0$ from the phase grating $G_1$,
λ=selected wavelength of the radiation,
$h_1$=web height of the phase grating $G_1$ in radiation direction,
n=index of refraction of the grating material of the phase grating.

Furthermore, it is stated that the line orientation of the gratings $G_0$ through $G_2$ should be fashioned so that the grating lines of all three gratings run parallel to one another. However, this should advantageously not be necessary if these grating lines are oriented parallel or perpendicular to the system axis S.

It has been shown, however, that grating/detector modules arranged at large fan angles show unsatisfactory results given an execution of such a grating-populated source/detector system in which the grating lines are aligned parallel to the system axis and a relatively wide detector is simultaneously used (thus a large fan angle perpendicular to the system axis occurs for the radiation beam that is used).

SUMMARY OF THE INVENTION

An object of the present invention is to improve x-ray CT systems of the above type for the generation of tomographical phase contrast or dark field exposures with regard to their power, and in particular to improve measurements that are implemented at large fan angles.

The invention is based on the insight that, given the design of the spacing conditions of the grating structures in the source/detector system operating as a Talbot interferometer, the geometric conditions described above are not sufficient and require a modification. The reason for this is because the grating period becomes ever smaller with increasing fan angle. If a grating surface (here the grating surface of a source grating or the surface of bands emitting more or less strong x-ray radiation at an anode) is considered from an increasingly flatter angle, the visible grating period (thus the grating period projected toward the observer) increasingly becomes more severely reduced. If the interference conditions of the Talbot interferometer should be maintained, the geometric conditions of the grating arrangement must also be adapted corresponding to the increasingly flatter observation angle (i.e. corresponding to a larger fan angle in the case of the CTs considered herein).

In the case of the CT system considered herein, this means that at least the distance between the grating structure at the source and the phase grating (corresponding to the grating period projected at the phase grating) must be reduced. The visible or projected grating period $P_0'(\phi_i)$ given the fan angle $\phi_i$ of a source grating structure with the actual grating period $p_0$ follows the relationship $p_0'(\phi_i) = p_0 \cos(\phi_i)$. The distance $I(\phi_i)$ between the grating structure at the source and the phase grating must be accordingly shortened according to the relationship $I(\phi_i) = I_0 \cos(\phi_i)$ with increasing fan angle $\phi_i$.

If the projected grating periods varying depending on the fan angle is considered from this viewpoint, the following geometric relationship results for the grating periods of the gratings that are used:

$$p_1(\varphi_i) = \frac{2p_2}{1 + \frac{p_2}{p_0}\cos(\varphi_i)},$$

with $p_0$ the grating period of the grating structure of the x-ray source, $p_1(\phi_i)$ the grating period of the considered phase grating at the fan angle $\phi_i$, and $p_2$ the grating period of the associated analysis grating.

With regard to the distance $d(\phi_i)$ between phase grating and analysis grating depending on the fan angle $\phi_i$, the condition $$d(\varphi_i) = \frac{l_0 D \cos(\varphi_i)}{l_0 \cos(\varphi_i) - D}, \text{ with } D = \frac{p_1^2}{8\lambda}$$

should be satisfied, with $I_0$ the distance between the grating structure of the x-ray source and the phase grating at the fan angle $\phi_0 = 0°$ and $p_1$ the grating period of the phase grating. $\lambda$ corresponds to the wavelength of the x-ray radiation to which the Talbot interferometer is tuned.

Based on this insight, the inventor is an improvement of an x-ray CT system having at least one source/detector system to generate tomographical phase contrast or dark field exposures, which system is arranged on a gantry rotatable around a system axis, wherein the source/detector system has an x-ray source with a grating structure that emits bands of emission maxima and emission minima of a generated x-ray radiation with a grating period, the bands being arranged like a grating, wherein a beam fan of x-rays expanded in two planes arises with a maximum fan angle in the rotation plane of the gantry and a Z-angle perpendicular to the rotation plane of the gantry, a detector arrangement with a number of grating/detector modules arranged parallel to one another, each module having (arranged one after the other in the beam direction) at least one phase grating that generates an interference pattern, and an analysis grating with directly connected detector with a number of detector elements to determine phase, average radiation intensity and amplitude of the average intensity of the radiation per detector element given relative displacement of one of the upstream grating structures, wherein the grating lines of all grating structures are aligned parallel to one another and parallel to the system axis.

The improvement according to the invention is in that the distance between the grating structure of the x-ray source and the phase grating of the respective grating/detector modules is adapted depending on the fan angle corresponding to a period of the grating structure of the x-ray source that is projected onto the grating/detector module at the respective fan angle.

With an alignment of the grating structure parallel to the system axis (and therefore perpendicular to the plane defined by the fan angle of the detector), the projected grating period of the source grating, or of the grating structure (shaped in bands) of the focal spot on the anode as actually viewed from the phase grating is thus taken into account depending on the respective observed fan angle, by an adaptation of the separation of the grating structures. Optimal interference conditions are hereby maintained over the entire utilized fan angle of a CT system, and significantly improved measurement results also arise given the same fan angles.

The grating structure of the x-ray source can advantageously be fashioned flat, and the grating/detector modules can advantageously be arranged such that, with regard to the distance between the x-ray source and the phase grating per grating/detector module, so that:

$$l_i = l_0 * \cos(\phi_i),$$

wherein $I_0$ corresponds to the distance between the x-ray source and the phase grating at the fan angle $\phi_0 = 0°$.

Additionally in accordance with the present invention, the grating periods of the utilized grating structures of phase and analysis gratings are adapted per grating/detector module depending on the fan angle and satisfy the following condition:

$$p_1(\varphi_i) = \frac{2p_2}{1 + \frac{p_2}{p_0}\cos(\varphi_i)},$$

wherein $p_0$ corresponds to the grating period of the grating structure $G_0$ of the x-ray source, $p_1(\phi_i)$ corresponds to the grating period of the i-th phase grating $G_{1,i}$ at the i-th fan angle $\phi_i$ and $p_2$ corresponds to the grating period of the analysis grating $G_2$.

It is also advantageous for the distance between phase grating and analysis grating to be adapted according to the invention per grating/detector module and the following condition is satisfied depending on the fan angle:

$$d(\varphi_i) = \frac{l_0 D \cos(\varphi_i)}{l_0 \cos(\varphi_i) - D}, \text{ with } D = \frac{p_1^2}{8\lambda},$$

wherein $I_0$ corresponds to the distance between the grating structure $G_0$ of the x-ray source and the phase grating $G_{1,0}$ at the fan angle $\phi_0 = 0°$, $p_1$ corresponds to the grating period of the phase grating $G_{1,i}$ and $\lambda$ corresponds to the wavelength of the x-ray radiation to which the system is tuned.

Furthermore, the detector of the at least one source detector system can advantageously be formed by a number of grating/detector modules connected together in the direction of the fan angle or—in particular given a particularly large number of rows—of at least two rows of grating/detector modules connected together in the direction of the fan angle.

The grating structure of the x-ray source can be designed as a flat focal spot and an absorption grating arranged in the beam path. Such a design is disclosed by F. Pfeiffer et al. in "Hard X-ray dark field imaging using a grating interferometer", Nature Materials, Vol. 7, pages 134 to 137, 01 Feb. 2008, (see in particular FIG. 1a) or in the aforementioned disclosure document DE 10 2006 015 358 A1.

Alternatively, however, the grating structure of the x-ray source can be formed by a number of band-shaped focal spots arranged in parallel. Such an embodiment is described in EP 1 803 398 A1.

In the last-cited embodiment of the grating structure of the x-ray source, it can furthermore be advantageous for the anode to be a rotating anode with a cylindrical surface as an anode surface, in which a number of depressions are introduced, with the rotation body of the rotating anode being composed of a first material and the surface in the region of the depressions being overlaid with a second material. For the formation of optimally strong band-shaped radiation maxima and minima, it is particularly advantageous for the materials to exhibit significant differences in the mass number, in particular for the second material to exhibit a higher mass number than the first material. The use of tungsten for the second material applied in the depressions is advantageous.

Additionally, given the use of a rotating anode with an alignment of the depressions with increased radiation intensity parallel to the rotation axis (or at least with a parallel component), the scanning of the detector that is used therewith is synchronized with the rotation of the rotating anode, such that the scanning of the detector (thus the integration interval of the measurement) occurs when the rotating depressions of the rotating anode are respectively in congruent position. For example, the rotation of the rotating anode can be detected by an optical or electromagnetic sensor, and the scanning of the detector can be correspondingly triggered.

DESCRIPTION OF THE PREFERRED EMBODIMENTS

Figure 1:
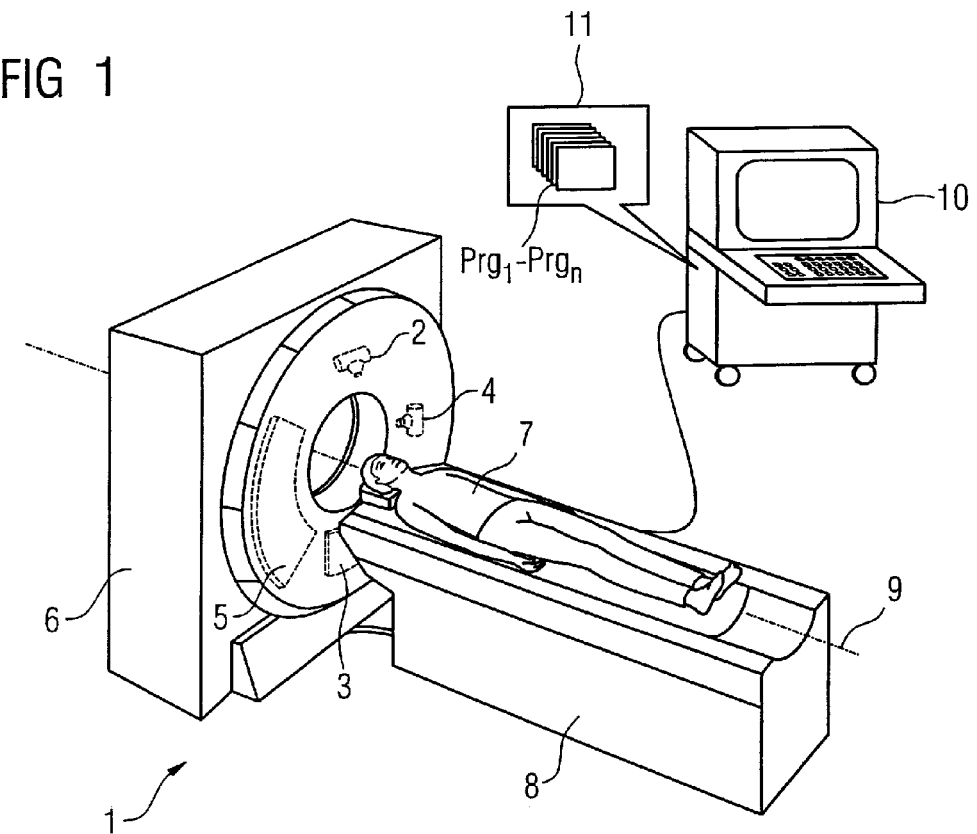
FIG. 1 shows the basic components of an x-ray CT system.

In the following the invention is described in detail with the figures, wherein only the features necessary to understand the invention are shown. The following reference characters and symbols are hereby used: 1: x-ray CT system; 2: x-ray source; 3: detector; 4: x-ray source; 5: detector; 6: gantry housing; 7: patient; 8: patient bed; 9: system axis; 10: control and computing system; 11: memory; 12: rotating anode; 13: source-side grating structure; 14: depressions; 15: second material; 16: electron emitters; 17: magnetic field; d: distance from the phase grating $G_1$ to the analysis grating $G_2$ in the fan beam geometry; $d^=$: distance form the phase grating $G_1$ to the analysis grating $G_2$ under parallel geometry; D: detector; $e^-$: electrons; F: focus/focal spot; $G_0$: source grating; $G_1$, $G_{1,i}$: phase grating; $G_2$, $G_{2,i}$: analysis grating; $h_i$: web height of the phase grating $G_1$ in the beam direction; $I_{med}$: median radiation intensity; $I_{amp}$: amplitude; $I_{amp}$: amplitude; I: distance from the source grating $G_0$ to the phase grating $G_1$; $I_0$: Talbot distance; n: index of refraction of the grating material of the phase grating; $p_0$: grating period of the source grating $G_0$; $p_0'$: projected grating period; $p_1$: grating period of the phase grating $G_1$; $p_2$: grating period of the analysis grating $G_2$; $Prg_1$-$Prg_2$: computer programs; S: radiation beam; $\lambda$: selected wavelength of the radiation; $\xi$: Z-angle; $\phi$: fan angle.

FIG. 1 shows an x-ray CT system 1 with modular grating/detector system designed according to the invention which is suitable for generation of tomographic x-ray phase contrast exposures, x-ray dark field exposures and even simple absorption exposures or combinations of these. The x-ray CT system consists of the housing 6 in which a gantry is located, on which gantry one or optionally multiple source/detector systems can be arranged. Located in the shown example are two x-ray sources 2 and 4 arranged at an angular offset of 90°, with respective detector systems 3 and 5 arranged opposite them. The x-ray sources can respectively consist of a combination of a simple x-ray tube with a source grating located in the beam path. The source grating is therefore an absorption grating which generates radiation minima (after the grating webs) and radiation maxima (after the grating gaps) arranged in bands and therefore forms a quasi-coherent radiation beam with sufficient dose power to examine larger examination subjects (for example a patient). Alternatively, the x-ray source can possess a structured anode surface on which radiation maxima and radiation minima arranged in bands arise due to the structure of the anode surface. Moreover, the possibility also exists to generate a band-shaped x-ray emission pattern via corresponding deflection of an electron beam.

The detector is of modular design, made up of a plurality of grating/detector modules, and each grating/detector module respectively possesses a phase grating and an analysis grating downstream in the beam path, wherein at least the distance between the grating structure on the side of the radiation source and the phase grating of each grating/detector module is individually set corresponding to the grating periods of the grating structure at the source that is projected onto the grating/detector module.

For examination, the examination subject (here a patient 7) can be displaced continuously or sequentially through the measurement field with the aid of a displaceable patient bed 8 along a system axis 9 around which the gantry rotates. The control, measurement and reconstruction of the tomographical image representations are hereby implemented via a control and computing system 10 in whose memory computer programs or programs modules $Prg_1$-$Prg_n$ are stored that execute control, measurement and reconstruction in a known manner upon operation.

Figure 2:
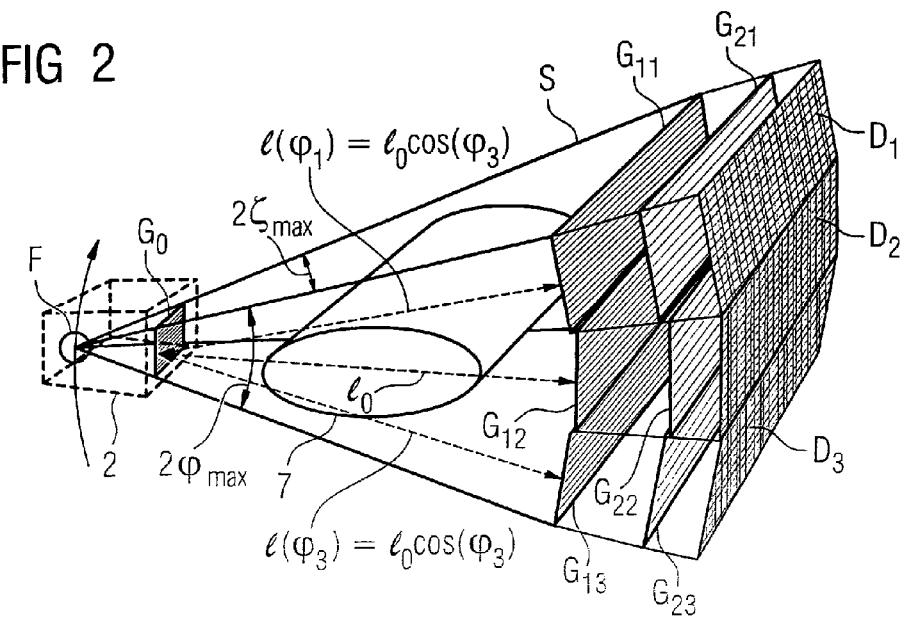
FIG. 2 shows an embodiment of the source/detector system of the invention in 3D view.

The modular design of a grating/detector system of a CT system according to the invention is schematically depicted in FIG. 2 with three grating/detector modules $G_{11}$, $G_{21}$, $D_1$ through $G_{13}$, $G_{23}$, $D_3$ in connection with an exemplary shown x-ray source 2 with expanded focus F and an absorption grating arranged as a source grating in the beam path to generate a quasi-coherent radiation as it is required for phase contrast measurement or dark field measurement. The radiation beam S radiated from the x-ray source 2 fans out in two planes standing perpendicular to one another, and the one hand by twice the Z-angle $2 \times \xi_{max}$ and on the other hand by twice the fan angle $2 \times \phi_{max}$, such that the radiated detector is covered as precisely as possible. The central grating/detector module $G_{12}$, $G_{22}$, $D_2$ is arranged such that it forms a classical Talbot distance $I_0$ between the source structured like a grating (here the source grating $G_0$) and the phase grating $G_{12}$. The grating/detector modules $G_{11}$, $G_{21}$, $D_1$ and $G_{13}$, $G_{23}$, $D_3$ standing at the edges see the source grating $G_0$ corresponding to their average fan angle $\phi_1$ or $\phi_3$ with a smaller grating period. Their separates are correspondingly reduced with $I(\phi_1) = I_0 * \cos(\phi_1)$ or, respectively, $I(\phi_3) = I_0 * \cos(\phi_3)$. In the present example, the distances between the phase gratings $G_{11}$, $G_{13}$ and the analysis gratings $G_{21}$, $G_{23}$ are also reduced so that the condition $$d(\varphi_i) = \frac{I_0 D \cos(\varphi_i)}{I_0 \cos(\varphi_i) - D}, \text{ with } D = \frac{p_1^2}{8\lambda}$$

is satisfied.

Figure 3:
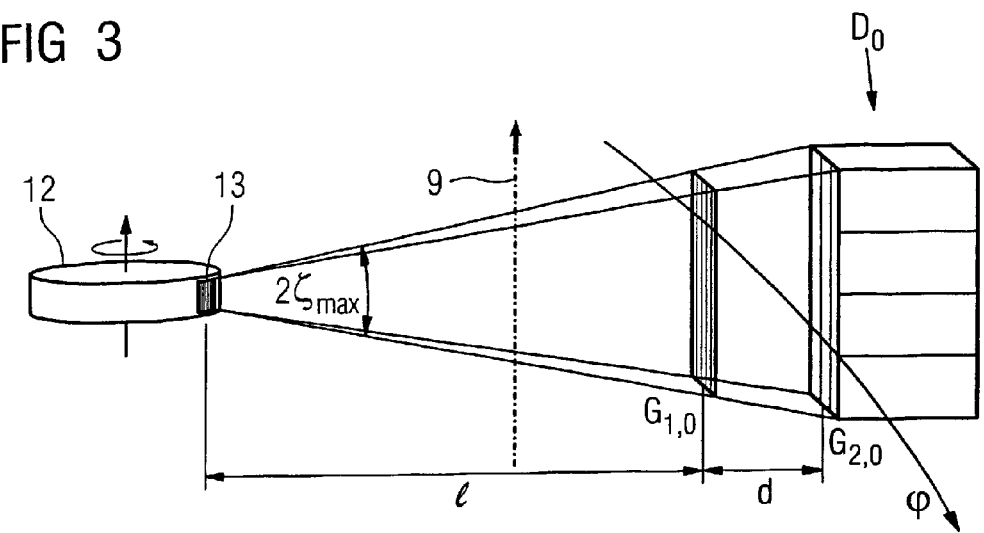
FIG. 3 shows the source/detector system of FIG. 2 in side view, perpendicular to the system axis.
Figure 4:
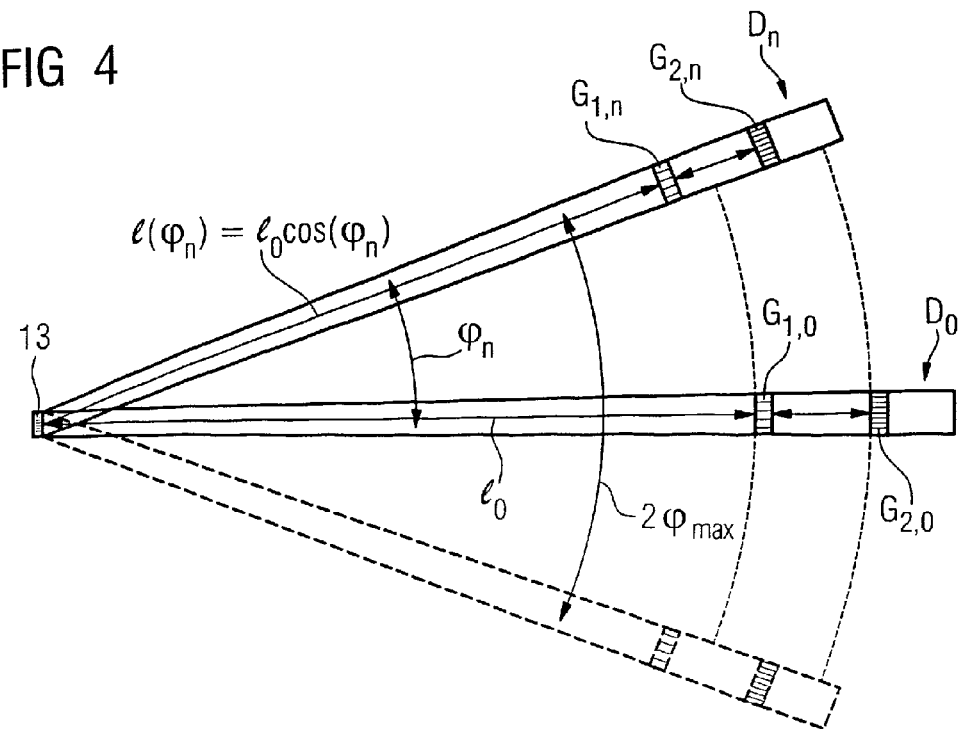
FIG. 4 shows the source/detector system of FIG. 2 in side view, parallel to the system axis.

For a better understanding, the modular design of the detector made up of grating/detector modules is shown in FIGS. 3 and 4, on the one hand in a lateral 3D view perpendicular to the system axis 9 with a view of a grating/detector module, and on the other hand in a view in the system axis direction with a view of one grating/detector module placed centrally and one placed at the edge.

A cylindrical rotating anode 12 on whose surface a focal spot a focal spot with a band pattern like a grating is fashioned with emission maxima and minima. The beam fan is fanned out by an angle of $2 \times \xi_{max}$ in the system axis direction. This fanning out runs in the direction of the bands of the focal spot 13 fashioned like a grating. A perspective change of the grating period hardly arises in this direction; in particular, the angle is also relatively small. The grating/detector module shown here, composed of a phase grating $G_{1,0}$, an analysis grating $G_{2,0}$ and four downstream detector elements (which are combined into one detector unit $D_0$) is based on a 4-line detector and corresponds to a centrally placed row of the detector. The distance between the grating structure of the focal spot 13 and the phase grating $G_1$ thus corresponds to the classical Talbot distance. d designates the distance between the phase grating $G_{1,0}$ and the analysis grating $G_{2,0}$.

Both the central grating/detector module $G_{1,0}$, $G_{2,0}$, $D_0$ from FIG. 3 and an n-th $G_{1,n}$, $G_{2,n}$, $D_n$ are recognizable in the plan view of FIG. 4. For better overview, the modules situated in between them are not shown. The central grating/detector module $G_{1,0}$, $G_{2,0}$, $D_0$ in which the grating structure 13 is not distorted in terms of perspective possesses a distance $I_0$ from the phase grating $G_{1,0}$. As can be seen, this illustration that this distance $I(\phi_n) = I_0 * \cos(\phi_n)$ at the grating/detector module $G_{1,n}$, $G_{2,n}$, $D_n$ standing at the edge is reduced by approximately 6% (here shown somewhat exaggerated) given a fan angle $\phi_n$ of approximately 20°. The interference conditions of the system are hereby adapted in the inventive manner to the periods $p_n = p_0 * \cos(\phi_n) = P_0 * \cos(20°)$ varied in perspective. The distance d also correspondingly varies between phase grating and analysis grating, such that the geometric conditions cited under FIG. 2 should be satisfied.

Figure 5:
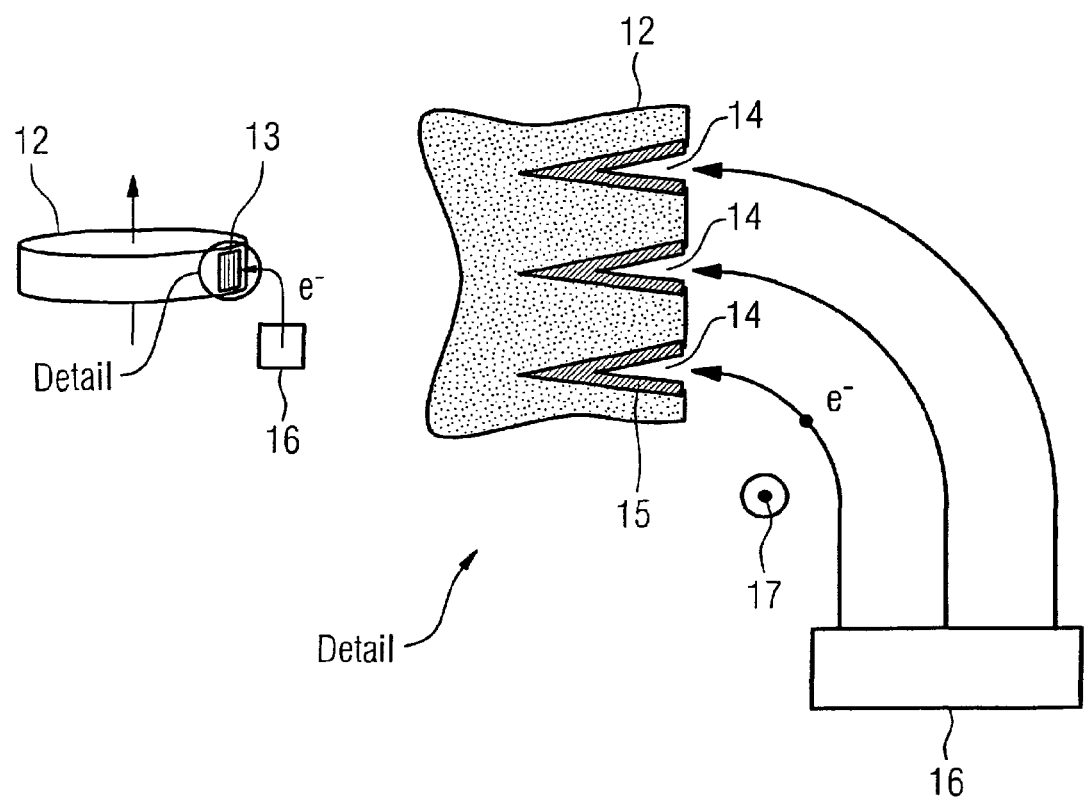
FIG. 5 shows a slotted rotating anode used in accordance with the invention.

Another individual representation of the rotating anode 12 from FIG. 3 with an electron emission 16 is additionally shown in FIG. 5, wherein the structure of the anode in the region of the focal spot is additionally shown in detail in section. Three indentations 14 of the anode surface are recognizable in the section representation, wherein the surfaces of the indentations 14 are overlaid with materials with high atomic number 15. The necessary band-shaped emission maxima and minima on the anode surface can be generated via this embodiment, such that the use of a source grating can be omitted. It is additionally noted that, in the embodiment of FIG. 5, a magnetic field 17 is used in order to more effectively defect the electrons e⁻ escaping at the electron emitter 16 from the detector surface relative to an electrical field that exists anyway due to the potential difference.

Overall, with the invention it is thus shown how, given a CT system with large fan angle, the disadvantage of a projected period varying at the edge of the detector can be compensated via corresponding modular design of the grating/detector system and adaptation of the distance between source-side grating structure and phase grating on the one hand and also adaptation of the other geometric conditions to obtain the interference conditions, and therefore uniformly good measurement results can be achieved over a wide angle range. This is achieved in that an x-ray CT system for generation of tomographical phase contrast or dark field exposures, with at least one grating interferometer with three grating structures arranged in succession in the radiation direction, is proposed in which a modular design of the second and third grating structures is realized, and the distance between the first grating structure of the x-ray source and the second grating structure of the respective grating/detector modules (fashioned as a phase grating) is adapted depending on the fan angle corresponding to a period of the grating structure of the x-ray source that is projected onto the grating/detector module at the respective fan angle.

Although modifications and changes may be suggested by those skilled in the art, it is the intention of the inventors to embody within the patent warranted hereon all changes and modifications as reasonably and properly come within the scope of his or her contribution to the art.

We claim as our invention:

1. An x-ray CT system comprising:
a source/detector system that generates tomographical phase contrast or dark field exposures, said source/detector system being mounted on a gantry rotatable around a system axis,
said source/detector system comprising an x-ray source having a grating structure that emits bands of emission maxima and emission minima of a generated x-ray radiation arranged like a grating, with a grating period ($p_0$), that emits a beam fan of x-rays widening in two places with a max fan angle ($2x\phi_{max}$) in the rotation plane of the gantry and a Z-angle ($2x\xi_{max}$) perpendicular to the rotation plane of the gantry;
said source/detector system comprising a detector arrangement with a plurality of grating/detector modules arranged in parallel, each module comprising, one after another in the beam direction, at least one phase grating ($G_{1,i}$) that generates an interference pattern, an analysis grating ($G_{2,i}$) with a directly connected detector with a plurality of detector elements to determine phase ($x_0$), average radiation intensity ($I_{med}$) and amplitude ($I_{amp}$) of the average intensity of the radiation per detector element given relative displacement of one of the upstream grating structures, the grating lines of all grating structures ($G_0$, $G_{1,i}$, $G_{2,i}$) being aligned parallel to one another and parallel to the system axis; and
a distance (I) between the grating structure ($G_0$) of the x-ray source and the phase grating ($G_{1,i}$) of the respective grating/detector modules being adapted depending on the fan angle corresponding to a period ($p_{0i}'$) of the grating structure ($G_0$) of the x-ray source that is projected onto the grating/detector module at the respective fan angle ($\phi_i$).

2. An x-ray CT system according to claim 1, wherein the grating structure ($G_0$) of the x-ray source is flat, and wherein the grating/detector modules are arranged, with regard to the distance ($I_i$) between the grating structure ($G_0$) of the x-ray source and the phase grating ($G_{1,i}$), with $$I_0 = I_0 * \cos(\phi_i),$$

wherein $I_0$ corresponds to the distance between the x-ray source ($G_0$) and the phase grating ($G_{10}$) at the fan angle $\phi_0 = 0°$.

3. An x-ray CT system according to claim 1 wherein the grating periods ($p_1$, $p_2$) of the grating structures ($G_1$, $G_2$) satisfy the following condition per grating/detector module, depending on the fan angle ($\phi_1$):

$$p_1(\varphi_i) = \frac{2p_2}{1 + \frac{p_2}{p_0}\cos(\varphi_i)},$$

wherein $p_0$ corresponds to the grating period of the grating structure $G_0$ of the x-ray source, $p_1(\phi_i)$ corresponds to the grating period of the i-th phase grating $G_{1,i}$ at the fan angle $\phi_i$, and $p_2$ corresponds to the grating period of the analysis grating $G_2$.

4. An x-ray CT system according to claims 1 wherein the distance ($d(\phi_i)$) between phase grating ($G_{1,i}$) and analysis grating ($G_{2,i}$) satisfies the following condition per grating/detector module, depending on the fan angle ($\phi_i$):

$$d(\varphi_i) = \frac{I_0 D \cos(\varphi_i)}{I_0 \cos(\varphi_i) - D}, \text{ with } D = \frac{p_1^2}{8\lambda}$$

wherein $I_0$ corresponds to the distance between the grating structure ($G_0$) of the x-ray source and the phase grating ($G_{1,0}$) at the fan angle $\phi_0 = 0°$, $p_1$ corresponds to the grating period of the phase grating ($G_{1,i}$) and $\lambda$ corresponds to the wavelength of the x-ray radiation to which the system is tuned.

5. An x-ray CT system according to claim 1 wherein the detector of the source/detector system comprises a row of grating/detector modules aligned in the direction of the fan angle.

6. An x-ray CT system according to claim 1 wherein the detector of the at least one source/detector system comprises at least two rows of grating/detector modules lined up in the direction of the fan angle.

7. An x-ray CT system according to claim 1 wherein the grating structure ($G_0$) of the x-ray source comprises a flat focal spot, and an absorption grating in the beam path.

8. An x-ray CT system according to claim 1 wherein the grating structure ($G_0$) of the x-ray source comprises a plurality of focal spots formed in bands and arranged parallel to one another.

9. An x-ray CT system according to claim 8, wherein the x-ray source comprises a rotating anode having a rotating body with a cylindrical surface as an anode surface having a plurality of depressions therein, said rotation body of the rotating anode consisting of a first material, and a second material overlaid on the surface in the region of the depressions.

10. An x-ray CT system according to the claim 9, wherein the second material has a higher mass number than the first material.

11. An x-ray CT system according to the claim 10, wherein the second material is tungsten.

12. An x-ray CT system according to claim 9 wherein the depressions are aligned parallel to, or with a component parallel to, the rotation axis of the rotating anode, and comprising a synchronization unit that synchronizes scanning of the detector with rotation of the rotating anode to cause scanning of the detector and thus an integration interval of a measurement to occur when the rotating depressions of the rotating anode are respectively in congruent position.

13. An x-ray CT system according to claim 12, comprising a rotation rate sensor that triggers scanning of the detector, mounted on the rotating anode.

* * * * *